United States Patent
Gilman

[11] Patent Number: 5,106,362
[45] Date of Patent: Apr. 21, 1992

[54] VENTED ABSORBENT DRESSING

[75] Inventor: Thomas Gilman, Mansfield, Mass.

[73] Assignee: The Kendall Company, Mansfield, Mass.

[21] Appl. No.: 337,591

[22] Filed: Apr. 13, 1989

[51] Int. Cl.⁵ .................. A61F 13/00; A61F 15/00
[52] U.S. Cl. ........................... 602/47; 602/59; 128/888
[58] Field of Search .............. 128/155, 888; 604/307

[56] References Cited

U.S. PATENT DOCUMENTS

| 2,443,140 | 6/1948 | Larsen | 128/888 |
| 4,399,816 | 8/1983 | Spangler | 128/888 |
| 4,541,426 | 9/1985 | Webster | 128/156 |

FOREIGN PATENT DOCUMENTS 2268504  4/1974  France ................... 128/335

Primary Examiner—Randall L. Green
Assistant Examiner—Paul Prebilic
Attorney, Agent, or Firm—Alvin Isaacs

[57] ABSTRACT

A dressing for a wound of a patient having, a base sheet for contacting the skin of the patient, with the base sheet having an opening for placement over the wound. The dressing has a vent providing controlled leakage of fluid along a path from the wound through the opening of the base sheet.

23 Claims, 5 Drawing Sheets

1

VENTED ABSORBENT DRESSING

BACKGROUND OF THE INVENTION

In the case of a draining wound, a transparent dressing, such as POLYSKIN (a trademark of the Kendall Company, Boston, Massachusetts for a thin elastomeric film carrying a layer of a medical grade pressure-sensitive adhesive) provides certain advantages such as a bacterial barrier, and a barrier to fluid. These advantages apply both to the case of protecting the wound from outside contaminants and protecting the patient's healthy skin from the wound exudate. In addition, such a dressing maintains a moist environment where desiccation can be detrimental. However, such dressings do not have the ability to handle wound fluid. Thus, the fluid builds up in a pressure bubble beneath the dressing, which tends to undermine the adhesive seal to the skin which increases the possibility of contamination to the wound by skin organisms.

SUMMARY OF THE INVENTION

A principal feature of the present invention is the provision of an improved dressing for a wound of a patient of simplified construction.

The dressing of the present invention comprises, a base sheet for contacting the skin of the patient, with the base sheet having an opening for placement over the wound. The dressing has vent means for providing controlled leakage of fluid along a path from the wound through the opening of the base sheet.

A feature of the present invention is that the dressing maintains a moist wound environment and prevents scab formation.

Another feature of the invention is that the dressing provides controlled leakage of excess wound fluid.

In one form, an absorbent fabric or other open-celled porous material may be placed over the vent means, and the dressing prevents adherence of the fabric to the wound.

Yet another feature of the invention is that the dressing permits leakage in a controlled manner, and minimizes the possibility of undermining the adhesive seal of the base sheet to the patient's skin.

A further feature of certain embodiments of the invention is that the dressing prevents bacteria from reaching the wound along the fluid path.

In one form, the vent means provides controlled leakage along a tortuous path from the wound through the opening of the base sheet while subjecting the fluid to an antimicrobial agent.

Thus, a feature of the invention is that the passage of fluid along the tortuous path assures prolonged contact of the fluid path from the source of bacteria to the wound with the antimicrobial agent in order to kill the bacteria.

Further features will become more fully apparent in the following description of the embodiments of this invention and from the appended claims.

DESCRIPTION OF THE PREFERRED EMBODIMENTS

Figure 1:
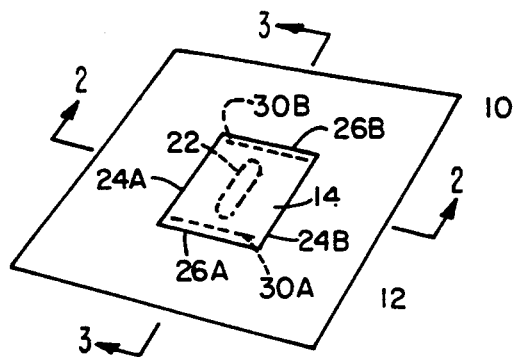
FIG. 1 is a perspective view of a dressing of the present invention.
Figure 2:
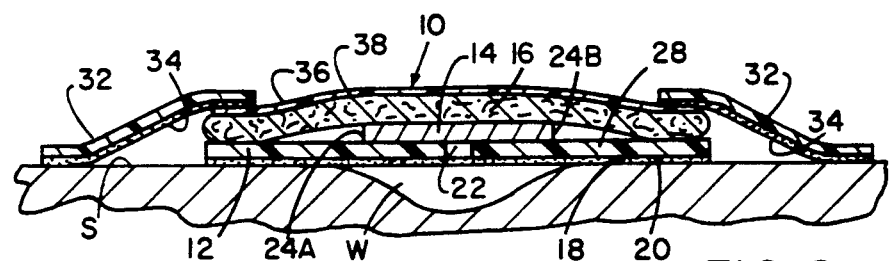
FIG. 2 is a sectional view taken substantially as indicated along the line 2—2 of FIG. 1.
Figure 3:
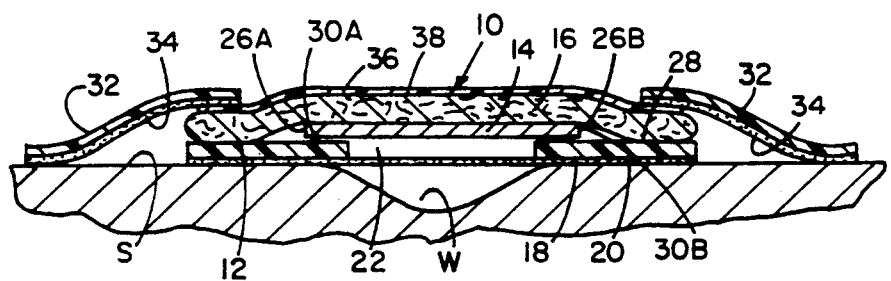
FIG. 3 is a sectional view taken substantially as indicated along the line 3—3 of FIG. 1.

Referring now to FIGS. 1-3, there is shown a dressing generally designated 10 having a base sheet 12, a vent sheet 14, and an absorbent layer 16. The base sheet 12 has an adhesive 18 on a front surface 20 of the base sheet 12 for securing the dressing 10 to the skin S of a patient. Useful adhesives include those per se known in the wound dressing art, e.g. rubber-based, acrylic, vinyl ether and hydrocolloid pressure-sensitive adhesives. As shown, the base sheet 12 has an opening 22 extending therethrough, and the base sheet 12 is secured to the patient with the opening 22 located over a wound W of the patient. The base sheet 12 may be constructed from a suitable moisture vapor permeable elastomer film, such as a polyurethane film.

The vent sheet 14 preferably has a generally rectangular shape. The vent sheet 14 has a pair of opposed side edges 24a and 24b, and a pair of opposed end edges 26a and 26b connecting the side edges 24a and 24b. As shown, the vent sheet 14 is secured to a back surface 28 of the base sheet 12 along sealing lines 30a and 30b, such as adhesive or heat sealing, extending along and adjacent the end edges 26a and 26b. In this configuration, the vent sheet 14 covers the opening 22 of the base sheet 12, with the side edges 24a and 24b of the vent sheet 14 being free of attachment from the base sheet 12. The vent sheet 14 may be constructed from a suitable water vapor-permeable material such as Pellethane (236380AE), a trademark of Upjohn, Kalamazoo, Mich., with the thickness of approximately one mil, with such a material constituting an elastomeric film. It may also, if desired, be constructed from a water vapor-impermeable material such as "Saran" (trademark of Dow Chemical).

As shown, the absorbent layer 16, such as a gauze sponge, is located over the back surface 28 of the base sheet 12 and over the vent sheet 14, and may have dimensions approximately the size of the base sheet 12. The absorbent layer 16 may be secured by suitable tape strips 32 having an adhesive 34 on a front surface thereof to the skin S of the patient. Although the absorbent layer 16 need not have a bacterial barrier, it preferably has a back film 36 of bacteria impervious material, such as the material of the base sheet 12, secured to a back surface 38 of the absorbent layer 16.

In use, the base sheet 12 is secured to the skin S of the patient with the opening 22 located over the wound W, and the absorbent layer 16 is secured over the vent sheet 14 by the tape strips 32. This configuration permits passage or migration of excess wound fluid through the opening 22 of the base sheet 12, past the side edges 24a and 24b of the vent sheet 14, and then into the absorbent layer 16 where the wound fluids are retained. The vent sheet 14 permits leakage in a controlled manner through the opening 22 in order to prevent the undermining of the adhesive seal of the adhesive layer 16 to the skin S of the patient. Also, the vent sheet 14, covering opening 22, helps insure a moist environment when excess fluid is wicked away from the wound by absorbent layer 16. It does this by reducing evaporation through opening 22 which would proceed more rapidly if the opening were not covered by the vent sheet. In addition, the film 36 of the absorbent layer 16 prevents the passage of bacteria to the absorbent layer 16 and the wound W. In addition, the dressing 10 prevents adherence of the absorbent layer 16 to the wound W since direct contact of the absorbent layer to the wound is obviated by the vent sheet. When the absorbent layer 16 becomes saturated by wound fluids, the tape strips 32 may be removed in order to replace a new absorbent layer 16 after which additional tape strips 32 are utilized to secure the new absorbent layer 16 in place on top of the base sheet 12. Thus, the absorbent layer 16 may be changed without the necessity of removing the base sheet 12 from the skin S of the patient, which would otherwise cause "tape stripping" by repeated removal of the dressing which irritates the skin. Thus, in accordance with the present invention, the dressing maintains a moist wound surface, prevents scab formation, prevents contact between wound fluid and intact skin, thereby protecting the intact skin from maceration.

Figure 4:
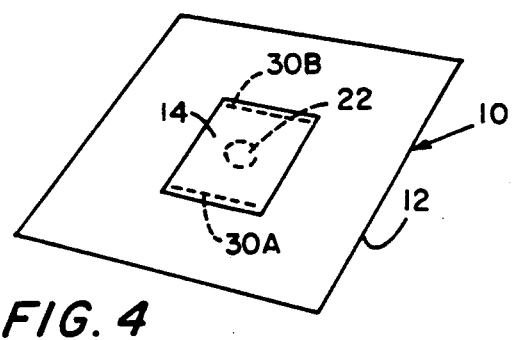
FIGS. 4 and 5 are perspective views of other embodiments of the dressing of the present invention.
Figure 5:
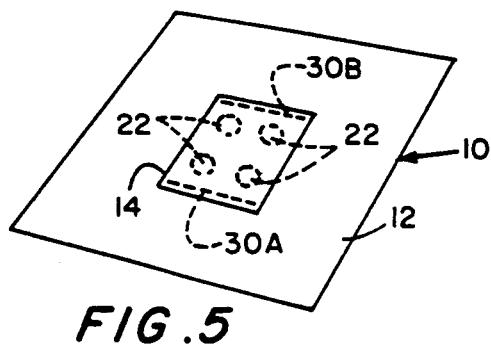

Although the opening 22 of the base sheet 12 was described as being elongated in connection with FIGS. 1-3, the opening 22 may be circular, or any other suitable shape, as shown in FIG. 4, and is preferably located centrally between the side edges 24a and 24b and end edges 26a and 26b of the vent sheet 14. Alternatively, as shown in FIG. 5, the base sheet 12 may have a plurality of openings 22 of any suitable shape located beneath the vent sheet 14.

Figure 6:
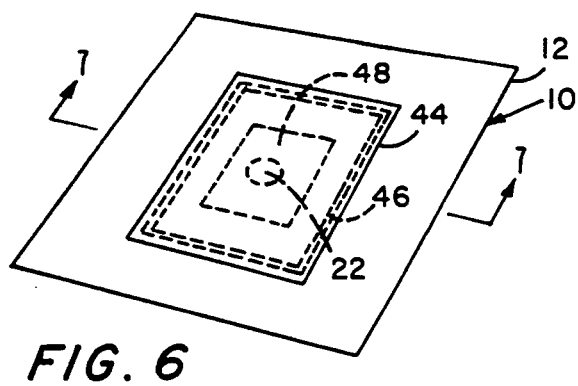
FIG. 6 is a perspective view of another embodiment of the dressing of the present invention.
Figure 7:
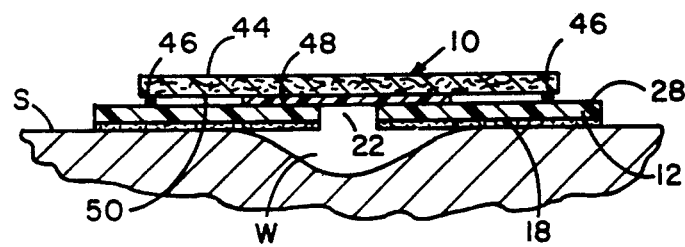
FIG. 7 is a sectional view taken substantially as indicated along the line 7—7 of FIG. 6.

Another embodiment of the present invention is illustrated in FIGS. 6 and 7, in which like reference numerals designate like parts. In this embodiment the base sheet 12 is substantially the same as described in connection with FIGS. 1-3. However, in this embodiment, the dressing 10 has an absorbent fine porosity fabric layer 44, such as a needle punched fabric, e.g. 60/40 rayon/polyester sold by National Felt, into which is introduced an antimicrobial agent, such as a salt of chlorhexidine. In order to impregnate the fabric layer 44 with the antimicrobial agent, the fabric layer 44 may be soaked in chlorhexidine solution and then air dried. The fabric layer 44 is secured around its periphery by suitable sealing lines 46, such as lines of adhesive, to the back surface 28 of the base sheet 12. The dressing 10 has a fluid impervious cover sheet 48 secured to a front surface 50 of the fabric layer 44. Suitable fluid-impervious sheet materials, e.g. polyolefinic materials, elastomers and the like are well known in the art and per se comprise no part of this invention. The cover sheet 48 is thus positioned intermediate the fabric layer 44 and the base sheet 12 and extends over the opening 22 of the base sheet 12. The cover sheet 48 is free of attachment to the base sheet 12, and serves as a vent, as previously described in connection with the vent sheet 14 of FIGS. 1-3.

In use, excess fluid from the wound W passes through the opening 22 of the base sheet 12 between the cover sheet 48 and base sheet 12 into the absorbent layer 44. Since this is the only fluid path to the wound W through the antimicrobial treated absorbent layer 44, microorganisms contained in the fluid that the layer 44 may absorb are killed by the antimicrobial agent, thus preventing passage of the microorganisms to the wound W of the patient. During use of the dressing 10, the cover sheet 48 serves as a roof over the opening 22 of the base sheet 12 to maintain the wound W in a moist state. Thus, the dressing 10 removes excess fluid from the wound W without the risk of contaminating the wound with outside bacteria.

Figure 8:
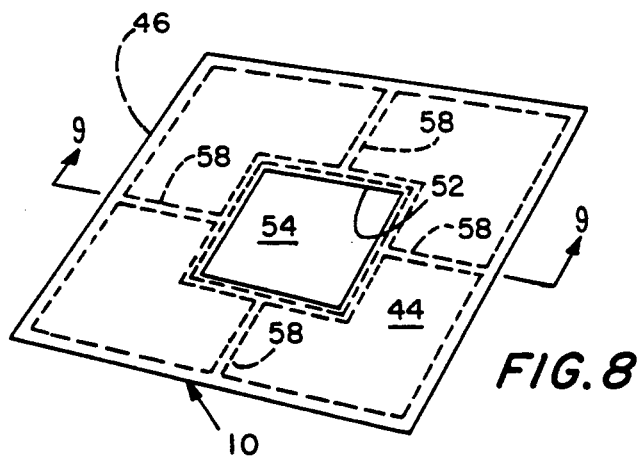
FIG. 8 is a perspective view of another embodiment of the dressing of the present invention.
Figure 9:
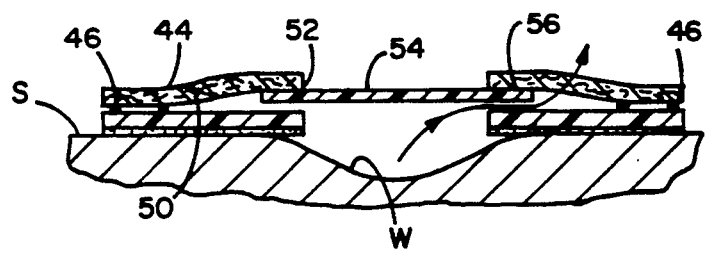
FIG. 9 is a sectional view taken substantially as indicated along the line 9—9 of FIG. 8.

Another embodiment of the present invention is illustrated in FIGS. 8 and 9, in which like reference numerals designate like parts. In this embodiment, the dressing has an absorbent layer 44 containing an antimicrobial agent constructed as previously described in connection with the absorbent layer 44 of FIGS. 6 and 7. However, in this embodiment, the absorbent layer 44 of fabric or other open-celled porous material has an opening 52 extending therethrough having dimensions of approximately the same size as the dimensions of the opening 22 of the base sheet 12, which in this case is substantially larger than the openings of the base sheet 12 previously described. Also, in this embodiment, the dressing 10 has a transparent cover sheet 54 which is positioned intermediate the layer 44 and the base sheet 12 and which extends across the opening 22 of the base sheet 12 and the opening 52 of the layer 44. The cover sheet 54 is secured by suitable means, such as adhesive 56 to the front surface 50 of the layer 44 peripherally around the opening 52 of the layer 44. In addition, the dressing 10 may have seal lines 58, such as adhesive, securing portions of the layer 44 to the base sheet 12 in order to provide stability between the layer 44 and the base sheet 12, and, as shown, the seal lines 58 may extend from the opening 52 of the layer 44 to outer margins of the layer 44.

In use, excess fluid from the wound W of the patient pass through the opening 22 of the base sheet 12 and intermediate the cover sheet 54 and base sheet 12 into the treated absorbent layer 44. As previously described in connection with FIGS. 6 and 7, the microorganisms contained in the fluid which the layer 44 may absorb are killed by the antimicrobial agent, such as the chlorhexidine, in layer 44, in order to prevent passage of microorganisms and possible contamination to the wound W. If desired, an absorbent layer may be placed upon the outer surface of the fabric layer 44. The absorbent dressing of FIGS. 8 and 9 has the advantages previously described in connection with FIGS. 6 and 7, and, in addition, the wound W may be viewed through the transparent cover sheet 54 without removing the dressing 10 from the skin S of the patient in order to monitor the condition of the wound W. In addition, the enlarged opening 22 of the base sheet 12 prevents the location of adhesive 18 over the central part of the dressing 10, such that removal of the dressing 10 will not damage the wound W by the adhesive layer 16.

Figure 10:
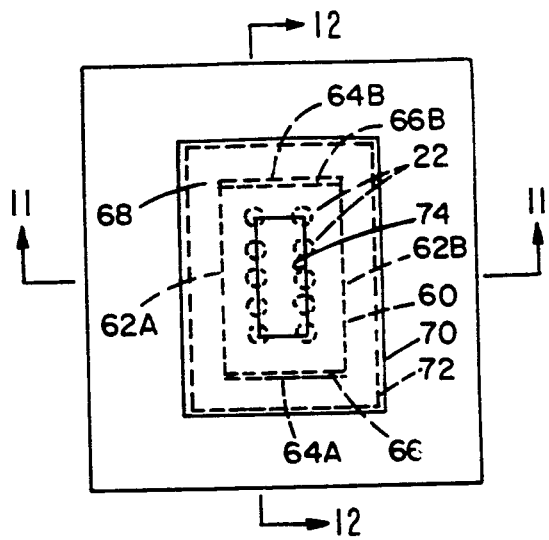
FIG. 10 is a top plan view of another embodiment of the dressing of the present invention.
Figure 11:
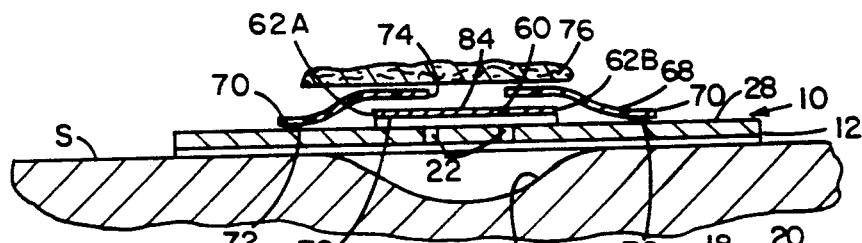
FIG. 11 is a sectional view taken substantially as indicated along the line 11—11 of FIG. 10.
Figure 12:
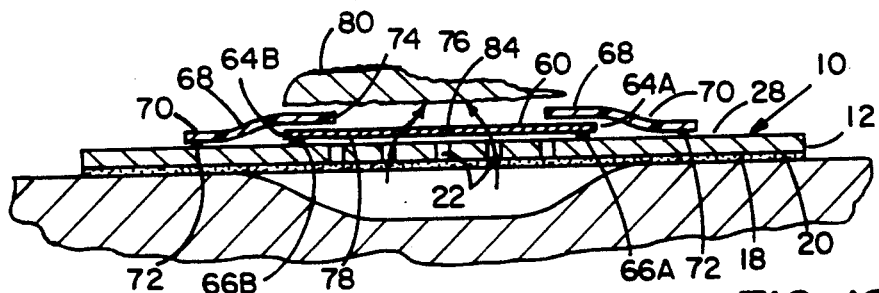
FIG. 12 is a sectional view taken substantially as indicated along the line 12—12 of FIG. 10.

Another embodiment of the present invention is illustrated in FIGS. 10–12, in which like reference numerals designate like parts. In this embodiment, the base sheet 12 is substantially the same as previously described in connection with FIGS. 1–3, and may have an opening 22 as shown. In this embodiment, the dressing 10 has a vent sheet 60 of transparent liquid impervious material. The vent sheet 60 has a pair of opposed side edges 62a and 62b, and a pair of opposed end edges 64a and 64b connecting the side edges 62a and 62b. The vent sheet 60 preferably has a rectangular shape, and is secured to the back surface 28 of the base sheet 12 by suitable sealing lines 66a and 66b, such as lines of adhesive or heat sealing, extending along and adjacent the end edges 64a and 64b. The vent sheet 60 is secured to the base sheet 12 in a configuration covering the opening 22 of the base sheet 12, and with the side edges 62a and 62b of the first vent sheet 60 being free of attachment to the base sheet 12.

The dressing 10 has a second vent sheet 68 of liquid impervious material located over the first vent sheet 60 and having peripheral margins 70 secured to the back surface 28 of the base sheet 12 by suitable sealing lines 72, such adhesive or heat sealing, extending around the first vent sheet 60. The second vent sheet 68 has an opening 74 located over the first vent sheet 60 with the dimensions of the second vent sheet opening 74 being smaller than the first vent sheet 60. A suitable absorbent layer 76 may be releasably secured in place over the second vent sheet 68. The first and second vent sheets 60 and 68 may be constructed from Pellethane (236380 AE), a trademark of Upjohn, Kalamazoo, Mich., with the thickness of approximately one mil, or a urethane film made by Thermedics, Inc. of Worchester, Mass.

In a preferred form, the first vent sheet 60 has an antimicrobial agent which may be located on a front surface 78 of the first vent sheet 60. It has been shown that when chlorhexidine discetate is co-cast with ethyl cellulose, a film results that releases chlorhexidine in a sustained way. The mechanism appears to be diffusion of chlorhexidine through the ethyl cellulose film, and may work as well with other salts of chlorhexidine, for example chlorhexidine gluconate. Such an antimicrobial agent may be placed on the front surface 78 of the first vent sheet 60.

In use, excess fluids from the wound W pass through the openings 22 of the base sheet 12, between the first vent sheet 60 and base sheet 12 around the side edges 62a and 62b and between a back surface 84 of the first vent sheet 60 and the second vent sheet 68 through the opening 74 of the second vent sheet 68 and into the absorbent layer 76. During this time, the second vent sheet 68 requires the wound fluid to travel a tortuous path from the source of bacteria to the wound, thereby insuring prolonged contact of the fluid with the source of antimicrobial agent to prevent external bacteria from reaching the wound W. In this manner, contamination of the wound W along the tortuous fluid path in this double vent structure is prevented along the tortuous path of wound fluid travel. The dressing 10 of this embodiment prevents scab formation, maintains a seal to the edge of the wound W which prevents wound fluid from coming in contact with skin S around the wound W, removes excess wound fluid from the wound W, and prevents external bacteria from reaching the wound W. In addition, the first vent sheet 60 is preferably transparent in order that the wound may be inspected without removal of the dressing 10 from the skin S of the patient, and the dressing 10 may be left in place until healing has been completed.

Optionally, as shown in FIG. 12, the absorbent layer 76 may have a back film 80 of bacteria impervious material, as previously described. In this form, the antimicrobial agent may be eliminated from the first vent sheet 60, and the film 80 of the absorbent layer 76 prevents passage of bacteria along the fluid path into the wound W.

Figure 13:
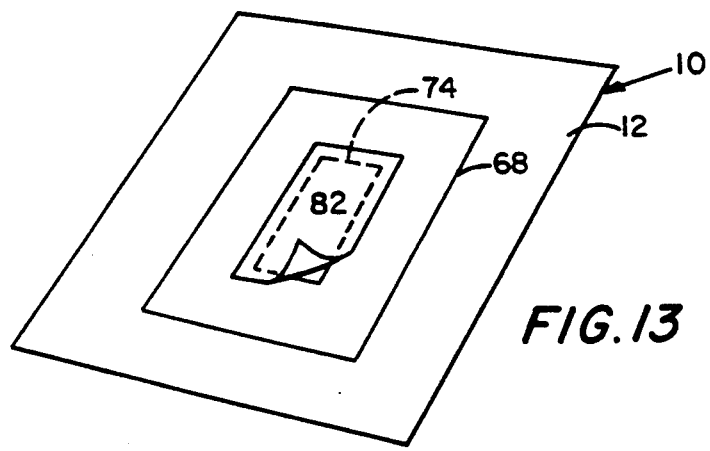
FIG. 13 is a perspective view of the dressing of FIG. 10 showing a tape strip being placed over an opening of the dressing.

In one form, as shown in FIG. 13, the second vent sheet 68 may have an outer silicone release coating located peripherally around the opening 74, and a suitable tape strip 82 having adhesive may be releasably secured to the outer surface of the second vent sheet 68 such that the strip closes the opening 74 of the second vent sheet 68 in order to temporarily seal the dressing 10 to prevent external fluids from reaching the wound W, such as when it is desired by the patient to bathe with the dressing 10 in place. The tape strip 82 may be removed from the second vent sheet 68 when it is desired to expose the opening 74 and resume operation of use of the dressing 10.

FIGS. 14–22 illustrate certain preferred embodiments of the invention wherein one or more channels are provided to facilitate fluid removal when excess pressure builds up in the wound.

Figure 14:
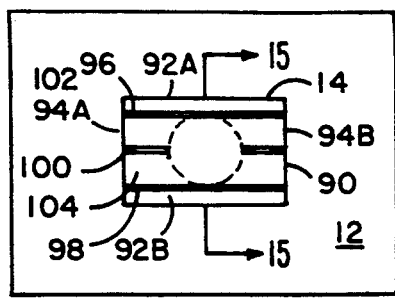
FIG. 14 is a plan view of another embodiment of the present invention.
Figure 15:
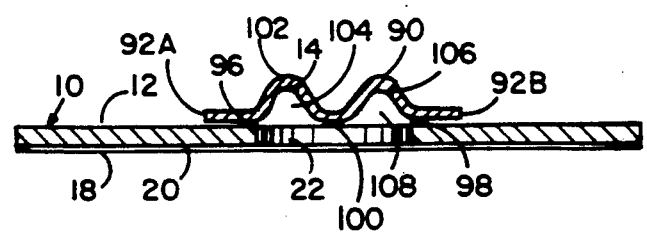
FIG. 15 is a sectional view taken substantially as indicated along the line 15—15 of FIG. 14.

As shown in FIGS. 14 and 15, in which like reference numerals deisgnate like parts, the base sheet 12 is substantially the same as previously described in connection with FIGS. 1–3. In this embodiment, the dressing 10 has a vent or cover sheet 90 covering the opening 22. The vent sheet 90 has a pair of side edges 92a and 92b, and a pair of end edges 94a and 94b connecting the side edges 92a and b. The vent sheet 90 preferably has a generally rectangular shape. The dressing has a pair of sealing lines 96 and 98, such as an adhesive or heat seals, on opposed sides of the opening 22 and extending between the end edges 94a and b, and a sealing line 100, such as an adhesive or a heat seal, located generally centrally between opposed sides of the opening 22, and extending between the opening 22 and the end edges 92a and b. The vent sheet 90 has a first upraised portion or fold 102 located between the sealing lines 96 and 100 defining a channel 104 extending between opening 22 and the end edges 94a and b. The vent sheet 90 also has a second upraised portion or fold 106 located between the sealing lines 98 and 100 defining a channel 108 extending between the opening 22 and the end edges 94a and b. In use, when excess pressure builds up in the wound, fluid will leak through by the channels 104 and 108 to the outside of the dressing 10 rather than undermine the adhesive 18 of the base sheet 12.

Figure 16:
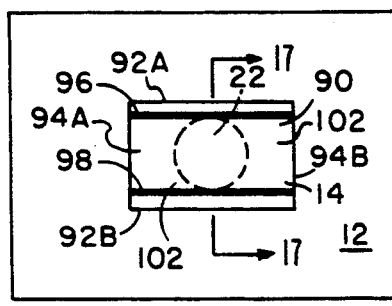
FIG. 16 is a plan view of another embodiment of the dressing of the present invention.
Figure 17:
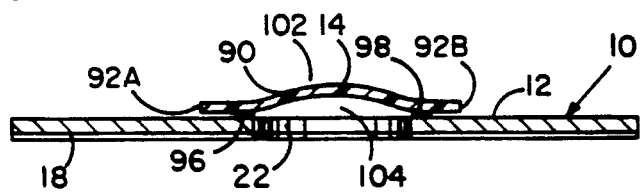
FIG. 17 is a sectional view taken substantially as indicated along the line 17—17 of FIG. 16.
Figure 18:
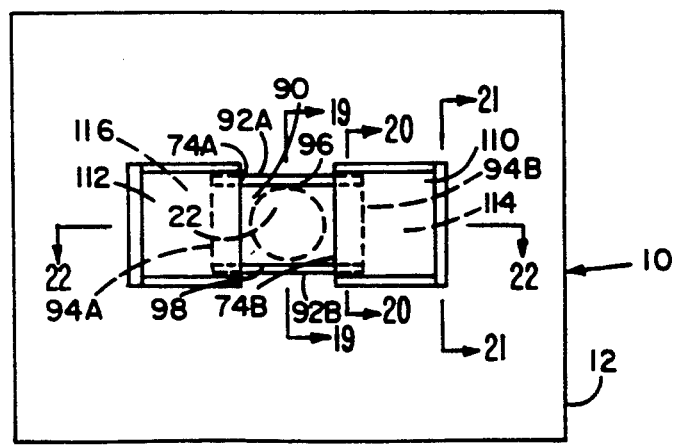
FIG. 18 is a plan view of another embodiment of a dressing of the present invention.
Figure 19:
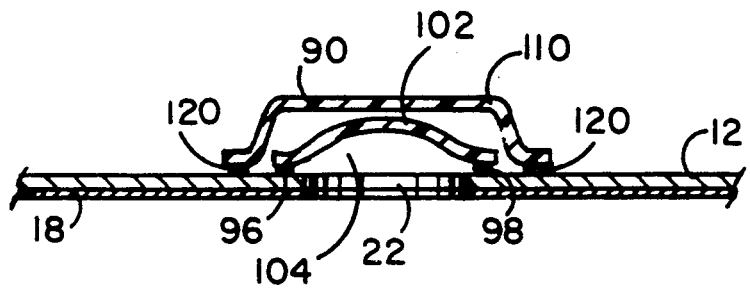
FIG. 19 is a sectional view taken substantially as indicated along the line 19—19 of FIG. 18.
Figure 20:
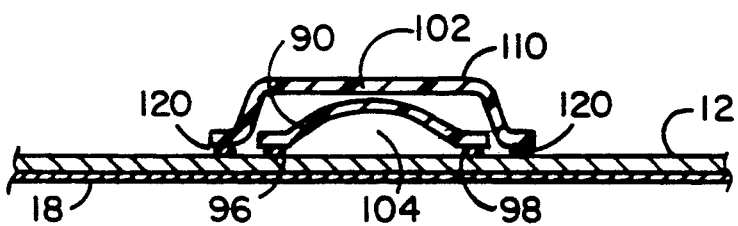
FIG. 20 is a sectional view taken substantially as indicated along the line 20—20 of FIG. 18.
Figure 21:
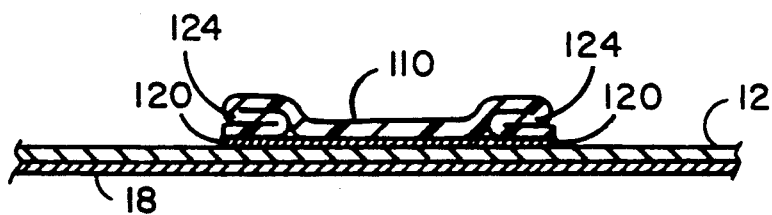
FIG. 21 is a sectional view taken substantially as indicated along the line 21—21 of FIG. 18.
Figure 22:
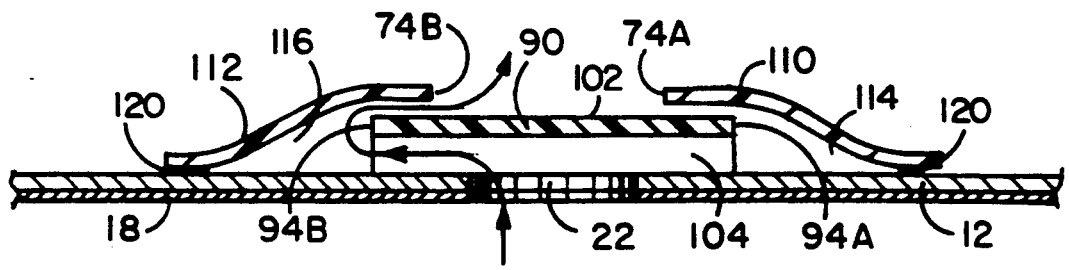
FIG. 22 is a sectional view taken along the line 22—22 of FIG. 18.

Another embodiment of the present invention is illustrated in FIGS. 16 and 17, in which like reference numerals designate like parts. In this embodiment, similar to the embodiment of FIGS. 14 and 15, the base sheet 12 is substantially the same as previously described in connection with FIGS. 1-3. In this embodiment, the dressing 10 also has a vent or cover sheet 90 covering the opening 22. The vent sheet 90 has a pair of side edges 92a and 92b, and a pair of end edges 94a and 94b connecting the side edges 92a and b. The vent sheet 90 preferably has a generally rectangular shape. The dressing has a pair of sealing lines 96 and 98, such as an adhesive or heat seals, on opposed sides of the opening 22 and extending between the end edges 94a and b. The vent sheet 90 has an upraised portion or fold 102 located between the sealing lines 96 and 98 defining a channel 104 extending between opening 22 and the end edges 94a and b. In use, when excess pressure builds up in the wound, fluid will leak through the channel 104 to the outside of the dressing 10 rather than undermine the adhesive 18 of the base sheet 12.

Another embodiment of the present invention is illustrated in FIGS. 18-22, in which like reference numerals designate like parts. In this embodiment, the base sheet 12 is substantially the same as previously described in connection with FIGS. 1-3. In this embodiment, the dressing 10 also has a vent or cover sheet 90 covering the opening 22, substantially as described in connection with FIGS. 16 and 17. The vent sheet 90 has a pair of side edges 92a and 92b, and a pair of end edges 94a and 94b connecting the side edges 92a and b. The vent sheet 90 preferably has a generally rectangular shape. The dressing has a pair of sealing lines 96 and 98, such as an adhesive or heat seals, on opposed sides of the opening 22 and extending between the end edges 94a and b. The vent sheet 90 has an upraised portion or fold 102 located between the sealing lines 96 and 98 defining a channel 104 extending between opening 22 and the end edges 94a and b.

The dressing 10 has a pair of opposed vent covers 110 and 112 secured to the base sheet 12 secured by a sealing line 120, such as adhesive or a heat seal, and defining cavities 114 and 116 to receive opposed ends 94a and b of the vent sheet 90. The vent covers 110 and 112 may have lower inwardly directed folds 124 adjacent an outer end of the vent covers 110 and 112. As shown, the vent covers 110 and 112 have opposed edges 74a and 74b located over the vent sheet 90, such that a tortuous path is defined between the opening 22, the channel 104, around the edges 94a and 94b of the vent sheet 90, as indicated by the direction of the arrow in FIG. 22, and between the vent covers 110 and 112 and the vent sheet 90. In this manner, a more reliable leak is obtained in order to prevent a possible seal of the vent sheet 90, while obtaining the advantages of the dressing described in connection with FIGS. 10-12.

By way of recapitulation, it will be seen that in the preferred embodiments of FIGS. 14-22, one or more channels for fluid removal are provided by having at least a portion of the cover sheet secured in raised relation to the base sheet. In the simplest form, the cover sheet is attached to the base sheet along two lines with the intermediate portion of the cover sheet between points of attachment being raised or elevated to define a channel through which fluid may leak. In other words, the linear dimension of the cover sheet between two attachment points will be greater than the linear dimension of the base sheet between points of attachment.

It is also contemplated that multiple raised portions may be provided with only two attachment lines, e.g. by corrugations in the cover sheet.

While, for purposes of illustration, the lines of attachment have been shown to be adjacent the opening in the base sheet, it will be appreciated that they may be elsewhere on the base sheet.

The foregoing detailed description is given for clearness of understanding only, and no unnecessary limitations should be understood therefrom, as modifications will be obvious to those skilled in the art.

What is claimed is:

1. A dressing for a wound of a patient, comprising:
   a base sheet for contacting the skin of the patient, said base sheet having an opening for placement over the wound, and means for securing the base sheet to the skin of a patient; and
   vent means for providing controlled leakage of fluid along a tortuous path from the wound through the opening of the base sheet, said vent means comprising a sheet material secured to said base sheet and covering said opening, said sheet material reducing evaporation through said opening while controlling said leakage of fluid along a tortuous path, thereby helping insure a moist environment for said wound.

2. The dressing of claim 1 including means for preventing bacteria from reaching the wound along said fluid path.

3. The dressing of claim 1 including means for absorbing the fluid passing from the vent means.

4. The dressing of claim 1 wherein the vent means comprises a vent sheet secured to the base sheet over the opening and having a raised portion defining at least one channel extending from the opening to an edge of the vent sheet.

5. The dressing of claim 1 including means for preventing bacteria from reaching the would along said fluid path.

6. The dressing of claim 1 including means for absorbing the fluid passing from the vent means.

7. The dressing of claim 1 wherein the vent means includes means for subjecting the fluid to an antimicrobial agent while passing along said tortuous path.

8. A dressing for a wound of a patient, comprising:
   a base sheet having adhesive on a front surface thereof for securing the base sheet to the skin of the patient, said base sheet having an opening for placement over the wound; and
   a vent sheet secured to the base sheet with the vent sheet overlying said opening, the vent sheet having a pair of side edges and a pair of end edges connecting the side edges, the vent sheet being secured to a back surface of the base sheet at a location adjacent the end edges with the side edges being free of attachment to the base sheet, said vent sheet providing controlled leakage of fluid from said wound while reducing evaporation through said opening, thereby helping to insure a moist environment for said wound.

9. The dressing of claim 8 wherein the vent sheet has at least one raised portion defining at least one channel extending from the opening to an edge of the vent sheet.

10. The dressing of claim 8 wherein the opposed ends are secured to a back surface of the base sheet.

11. The dressing of claim 8 wherein said opening is elongated and extends toward said opposed ends.

12. The dressing of claim 8 wherein said opening is generally circular, and is generally centrally located between said sides and ends of the vent sheet.

13. The dressing of claim 8 including an absorbent layer positioned over a back surface of the vent sheet.

14. The dressing of claim 13 wherein said absorbent layer includes a bacteria impervious layer.

15. The dressing of claim 8 wherein said vent sheet has a generally rectangular shape.

16. The dressing of claim 8 wherein said base sheet has a plurality of openings located beneath the vent sheet.

17. The dressing of claim 8 wherein the vent sheet comprises a water swellable elastomer material.

18. The dressing of claim 17 wherein the vent sheet comprises an amide ether block copolymer.

19. The dressing of claim 1 including a fabric layer secured over a back surface of the base sheet.

20. The dressing of claim 19 wherein the fabric layer contains an antimicrobial agent.

21. The dressing of claim 19 including the sheet material comprising the vent means is positioned intermediate the base sheet and fabric layer.

22. The dressing of claim 21 wherein the sheet material is secured to the front surface of the fabric layer facing the base sheet.

23. The dressing of claim 19 wherein the fabric layer is secured to a back surface of the base sheet peripherally around the fabric layer.

* * * * *